(12) United States Patent
Funahashi et al.

(10) Patent No.: US 8,790,690 B2
(45) Date of Patent: Jul. 29, 2014

(54) PATCH AND PATCH PREPARATION

(75) Inventors: Miki Funahashi, Ibaraki (JP); Atsushi Hamada, Ibaraki (JP); Tsuyoshi Kasahara, Ibaraki (JP); Jun Ishikura, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 343 days.

(21) Appl. No.: 12/458,627

(22) Filed: Jul. 17, 2009

(65) Prior Publication Data

US 2010/0015210 A1    Jan. 21, 2010

(30) Foreign Application Priority Data

Jul. 17, 2008  (JP) .................................. 2008-186561

(51) Int. Cl.
*A61K 9/70* (2006.01)
*A61L 15/16* (2006.01)
*B32B 27/06* (2006.01)

(52) U.S. Cl.
USPC ........................... 424/449; 424/448; 428/343

(58) Field of Classification Search
None
See application file for complete search history.

(56) References Cited

U.S. PATENT DOCUMENTS

| | | | | |
|---|---|---|---|---|
| 3,961,124 | A * | 6/1976 | Matton | 442/103 |
| 5,760,135 | A * | 6/1998 | Korpman et al. | 525/95 |
| 6,117,447 | A | 9/2000 | Nakano et al. | |
| 2003/0130427 | A1 | 7/2003 | Cleary et al. | |
| 2006/0019105 | A1* | 1/2006 | Vick et al. | 428/447 |
| 2007/0051376 | A1* | 3/2007 | Kulichikhin et al. | 128/894 |
| 2008/0118725 | A1 | 5/2008 | Iwao et al. | |
| 2008/0138388 | A1 | 6/2008 | Aida et al. | |
| 2010/0015209 | A1 | 1/2010 | Funahashi et al. | |
| 2011/0056609 | A1 | 3/2011 | Iwao et al. | |

FOREIGN PATENT DOCUMENTS

| | | |
|---|---|---|
| CN | 1226422 | 8/1999 |
| CN | 101194898 | 6/2008 |
| EP | 0 922 453 | 6/1999 |
| EP | 1925300 | * 11/2007 |
| EP | 1 925 300 | 5/2008 |
| JP | 03-127727 | 5/1991 |
| JP | 10-151185 | 6/1998 |
| JP | 11-228395 | 8/1999 |
| JP | 2006-306749 | 11/2006 |
| JP | 2010-43065 | 2/2010 |

OTHER PUBLICATIONS

Extended European Search Report issued Mar. 30, 2010 in European application corresponding to present U.S. application.
Chinese Office Action issued Jan. 16, 2013 in corresponding Chinese Application No. 200910139959.2, with English language translation thereof.
Chinese Office Action issued Apr. 18, 2012 in corresponding Chinese Application No. 200910139959.2 (with English translation).
Office Action drafted Apr. 26, 2013 in corresponding Japanese Application No. 2009-162063, with English language translation thereof.

* cited by examiner

*Primary Examiner* — Brian-Yong Kwon
*Assistant Examiner* — Jennifer A Berrios
(74) *Attorney, Agent, or Firm* — Wenderoth, Lind & Ponack, L.L.P.

(57) ABSTRACT

A patch containing a support and an adhesive layer formed on at least one surface of the support, wherein the adhesive layer contains an elastomer obtained by crosslinking a polymer having a butadiene skeleton in the presence of organic peroxide, wherein the patch has good adhesion property and maintain this quality for a long time.

1 Claim, No Drawings

PATCH AND PATCH PREPARATION

TECHNICAL FIELD OF THE INVENTION

The present invention relates to a patch and a patch preparation. More particularly, the present invention relates to a patch and a patch preparation having a superior skin adhesion force, which leave less adhesive residue on the skin.

BACKGROUND OF THE INVENTION

Patch is a convenient and effective dosage form for wound protection or administration of a drug to the body. The patch is requested to stably maintain the quality for a long time and have good adhesion property.

As a patch having such adhesion property, for example, patent document 1 and patent document 2 disclose patches having an adhesive layer comprised of a crosslinked rubber component having a functional group. In Example 4 of patent document 1, it is described with regard to such patch that oozing of an adhesive in 3 mm or less was observed in the peripheral area of a test piece. Thus, the patches are presumed to have insufficient cohesion force. Moreover, the patches of these documents may have unsatisfactory stability in patch quality due to the presence of the functional group in the rubber component. As shown above, none of the conventional patches sufficiently meet the above-mentioned requirements.
non-patent document 1: JP-A-03-127727
non-patent document 2: JP-A-10-151185

DISCLOSURE OF THE INVENTION

Problems to be Solved by the Invention

The present invention has been made in view of the above-mentioned situation and aims to provide a patch having good adhesion property and capable of stably maintaining the quality for a long time.

Means of Solving the Problems

Accordingly, the present invention provides the following.
(1) A patch comprising a support and an adhesive layer formed on at least one surface of the support, wherein the adhesive layer comprises an elastomer obtained by crosslinking polymers having a butadiene skeleton in the presence of organic peroxide.
(2) The patch of (1), wherein the above-mentioned adhesive layer comprises an elastomer obtained by crosslinking the above-mentioned polymers having a butadiene skeleton in the presence of the above-mentioned organic peroxide and a tackifier.
(3) The patch of (1) or (2), wherein the above-mentioned adhesive layer further comprises an organic liquid component.
(4) The patch of any of (1)-(3), wherein the above-mentioned polymer having a butadiene skeleton is polybutadiene.
(5) A patch preparation comprising the patch of any of (1) to (4) and a drug in the adhesive layer of the patch.

Effect of the Invention

According to the present invention, a patch superior in the skin adhesion force, which leaves less adhesive residue on the skin and stably maintains the quality for a long time, can be obtained. Accordingly, the patch of the present invention is suitable for adhesion to the skin of mammals. In addition, when the patch of the present invention is used for, for example, a patch preparation, an undesirable reaction between a drug and an adhesive composition can be reduced while maintaining good adhesion property, and the quality of the drug can be stably maintained for a long time.

BEST MODE FOR CARRYING OUT THE INVENTION

A preferable embodiment of the present invention is shown below.

The patch of the present invention comprises a support and an adhesive layer formed on at least one surface of the support, wherein the adhesive layer comprises an elastomer obtained by crosslinking polymers having a butadiene skeleton in the presence of organic peroxide.

Therefore, the adhesive layer contains an elastomer having a hydrocarbon chain with a comparatively high molecular weight, and affords an adhesive force and a cohesion strength preferable for a patch.

Moreover, since a polymer having a butadiene skeleton is used as a basic polymer in the present invention, a functional group for crosslinking is not necessary, the quality can be stably maintained for a long time during production and storage of the patch. Moreover, various basic polymers can be selected without limitation by the introduced functional groups, thus increasing the degree of freedom in selection of the basic polymers.

While the support to be used in the present invention is not particularly limited, a support substantially impermeable to the components in the adhesive layer, for example, adhesive, additive, drug and the like, namely, a support that does not permit them to pass through the support and be lost from the back face thereof, is preferable.

Examples of such support include single films of polyester, nylon, Saran (registered trade mark), polyethylene, polypropylene, polyvinyl chloride, ethylene-ethyl acrylate copolymer, polytetrafluoroethylene, Surlyn (registered trade mark), metal foil and the like, a laminate film thereof and the like. While the thickness of the support is not particularly limited, it is generally 10-500 μm, preferably 10-200 μm.

Among those, to improve the adhesion force (anchoring force) between the support and the adhesive layer, the support is preferably a laminate film of non-porous type plastic film recited above and a porous film. In this case, an adhesive layer is preferably formed on the porous film side.

As such porous film, one capable of improving the anchoring force with an adhesive layer is employed. Specifically, paper, woven fabric, non-woven fabric, knitted fabric, mechanically perforated sheet and the like can be mentioned. From the aspects of handling property and the like, paper, woven fabric and non-woven fabric are particularly preferable from among those.

In consideration of improvement of anchoring force, flexibility of the whole patch preparation and adhesion operability and the like, a porous film having a thickness of 10-200 μm is employed. In the case of a thin preparation, such as a plaster type and an adhesive tape type, one having a thickness of 10-100 μm is employed.

When woven fabric or non-woven fabric is used as a porous film, the fabric weight thereof is not particularly limited. It is generally 5-30 g/m², preferably 6-15 g/m².

In the present invention, the most preferable support is a laminate film of a 1.5-6 μm-thick polyester film (preferably, polyethylene terephthalate film) and a polyester (preferably, polyethylene terephthalate) non-woven fabric having a fabric weight of 6-12 g/m².

In the adhesive layer, a polymer having a butadiene skeleton is used as a basic polymer in the present invention, and the basic polymer preferably has a hydrocarbon chain, from the aspects of stability. When a polymer having a butadiene skeleton is used as a basic polymer, an elastomer formed by crosslinking has a hydrocarbon chain having a comparatively high molecular weight, and can impart skin adhesion force and cohesion force necessary for a patch to the adhesive layer. In addition, the elastomer formed by crosslinking has a structure wherein hydrocarbon chains are intricately entangled three-dimensionally. As a result, a cohesion force sufficient for a patch can be imparted to the adhesive layer.

Particular examples of the basic polymer include polybutadiene, styrene-butadiene block copolymer (hereafter "SB"), styrene-butadiene-styrene block copolymer (hereafter "SBS") and the like.

For example, when SB or SBS is used as a basic polymer, a high cohesion strength can be preferably imparted to an adhesive layer. Particularly, SBS affords an adhesive layer superior in cohesion strength due to its molecular structure.

From the aspects of reactivity and the like, moreover, polybutadiene is preferable as a basic polymer.

In the present invention, one or more kinds of basic polymers can be used in combination according to the object.

While the weight average molecular weight of the above-mentioned basic polymer is not particularly limited, it is preferably 50,000-5,000,000. The weight-average molecular weight means a value measured by gel permeation chromatography under the following conditions.

analysis conditions
GPC apparatus: HLC8120 (manufactured by Tosoh Corporation)
column: TSKgel GMH-H(S) (manufactured by Tosoh Corporation)
standard: polystyrene
eluent: tetrahydrofuran flow rate: 0.5 ml/min
measurement temperature: 40° C.
detector: differential refractometer Organic peroxide is not particularly limited, and those known per se which are generally used in the field of polymerchemical can be used. For example, diacyl peroxide (e.g., dibenzoyl peroxide, diisobutyryl peroxide, di(3,5,5-trimethylhexanoyl) peroxide, dilauroyl peroxide, disuccinic acid peroxide), peroxy esters (e.g., 1,1,3,3-tetramethylbutyl peroxy-2-ethylhexanoate, 2,5-dimethyl-2,5-di(2-ethylhexanoylperoxy)hexane), t-hexyl peroxy-2-ethylhexanoate, t-butyl peroxy-2-ethylhexanoate), ketone peroxide (e.g., methylethylketone peroxide), peroxyketal (e.g., 1,1-di(t-butylperoxy)cyclohexane), hydroperoxide (e.g., p-mentan hydroperoxide), dialkyl peroxide (for example, dicumyl peroxide), peroxydicarbonate (e.g., di-n-propylperoxydicarbonate) and the like can be mentioned.

Of these, from the aspects of reactivity, diacyl peroxide (particularly dibenzoyl peroxide) and peroxy ester (particularly 1,1,3,3-tetramethylbutyl peroxy-2-ethylhexanoate) are preferable. Particularly, diacyl peroxide is preferable, since it reacts with a basic polymer, and produces an elastomer which has substituent selected from alkyl, phenyl, acyl, benzoyl, acyloxy and benzoyloxy, each of which is optionally substituted. Alternatively, peroxy ester reacts with a basic polymer, and produces an elastomer which has substituent selected from alkyl, alkoxy, phenyl, acyl, benzoyl, acyloxy and benzoyloxy, each of which is optionally substituted.

The content of such organic peroxide is preferably 0.15-0.375 parts by weight per 100 parts by weight of the basic polymer. When it is less than 0.15 parts by weight, the cohesion strength of the adhesive layer tends to be insufficient, and when it exceeds 0.375 parts by weight, the adhesive layer becomes hard and the adhesive force and the soft feeling tend to decrease.

In the present invention, a large amount of other components may be added to an adhesive solution so that the adhesive layer will contain a large amount of other components. When, for example, a large amount of a tackifier is added as other component, the basic polymer is crosslinked in the presence of organic peroxide and, during formation of a three-dimensional net-like molecular structure as an elastomer, the tackifier is taken into its structure, whereby a large amount of tackifier can be contained in the adhesive layer. Consequently, the balance between adhesive force and cohesion strength is considered to be improved. Furthermore, the patch of the present invention can more improve adhesive force and tackiness during adhesion to the skin. In this case, even when the patch of the present invention is adhered to the skin and later detached, the possibility of leaving the adhesive layer on the skin surface is small.

As the tackifier, those known in the field of patch is appropriately selected and used. Examples of the tackifier include petroleum resin (e.g., aromatic petroleum resin, aliphatic petroleum resin), terpene resin, rosin resin, coumaroneinden resin, styrene resin (e.g., styrene resin, α-methylstyrene), hydrogenated petroleum resin (e.g., alicyclic saturated hydrocarbon resin) and the like. Among these, alicyclic saturated hydrocarbon resin is preferable since other compound in the adhesive layer, for example, organic liquid component, drug and the like, shows good preservation stability.

Tackifiers can be used in a combination of one or more kinds thereof. When two or more kinds are used in combination, for example, resins having different kinds and softening points may be combined.

In the present invention, while the ratio of the weight (a) of the basic polymer to the weight (b) of the tackifier ((a):(b)) is not particularly limited, it is preferably 3.0:1-1:2.0, more preferably 2.5:1-1:1.75. When the ratio of the weight (a) of the basic polymer is higher than this ratio, the adhesive force of the adhesive layer tends to decrease, the cohesion strength tends to be too high and the soft feeling tends to decrease. When the ratio of the weight (b) of the tackifier is higher than this ratio, the adhesive layer tends to be too soft to create stickiness.

It is also possible to add, for example, a large amount of organic liquid component as other component to the adhesive solution so that the adhesive layer will contain a large amount of an organic liquid component. As a result, the patch of the present invention can provide a soft feeling upon adhesion to the skin, and low irritation upon detachment from the skin. In this case, even when the patch of the present invention is released after adhesion to the skin, the possibility of the adhesive layer remaining on the skin surface is small. In addition, when the adhesive layer contains the below-mentioned drug, the transdermal absorption thereof can be promoted.

As the organic liquid component, a hydrophobic liquid component is preferable, such as fatty acid alkylester, from the aspect of compatibility with the adhesive layer.

Examples of the fatty acid alkylester include fatty acid alkylester comprised of higher fatty acid having 12-16 carbon atoms, preferably 12-14 carbon atoms, and lower monovalent alcohol having 1-4 carbon atoms. The above-mentioned higher fatty acid includes lauric acid (C12), myristic acid (C14) or palmitic acid (C16), preferably myristic acid. Examples of the above-mentioned monovalent alcohol include methyl alcohol, ethyl alcohol, propyl alcohol, butyl alcohol and the like, preferably isopropyl alcohol. Accordingly, preferable fatty acid alkyl ester is isopropyl myristate. The organic liquid components may be used in combination of one or more kinds thereof.

The content of organic liquid component is preferably 5-300 parts by weight, more preferably 50-170 parts by weight, per 100 parts by weight of the basic polymer. When the content of organic liquid component is less than 5 parts by weight, a superior soft feeling is imparted to the adhesive layer and, when the adhesive layer contains a drug, a high transdermal proabsorptive effect can be obtained. When it is not more than 50 parts by weight, a superior soft feeling is imparted to the adhesive layer and, when the adhesive layer contains a drug, a high transdermal proabsorptive effect can be advantageously obtained while suppressing a decrease in the adhesive force and cohesion force of the whole adhesive layer.

In the present invention, moreover, a patch preparation can also be produced by adding a drug to the adhesive layer. As mentioned above, since a basic polymer does not require a functional group for crosslinking, an undesirable reaction of the drug can be suppressed in the adhesive layer, thus contributing to the stability of the drug. In addition, an undesirable reaction of the functional group of the basic polymer and a drug does not need to be considered, thus increasing the degree of freedom in design of the patch.

The drug here is not particularly limited, and one permitting administration to mammals such as human and the like through the skin thereof, i.e., a transdermally absorbable drug is preferable. Specific examples of such drug include general anesthetics, hypnotic sedatives, antiepileptic drugs, antipyretic analgesic antiphlogistic drugs, anti-vertiginous drugs, psychoneurotic drugs, topical anesthetics, skeleton muscle relaxants, autonomic drugs, antiepileptic drugs, anti-parkinsonian drugs, anti-histamine drugs, cardiac stimulants, drugs for arrhythmia, diuretics, hypotensive drugs, vasoconstrictors, coronary vasodilators, peripheral vasodilators, arteriosclerosis drugs, drugs for circulatory organ, anapnoics, antitussive expectorants, hormone drugs, external drugs for mattery diseases, analgesic-antipruritic-styptic-antiphlogistic drugs, drugs for parasitic dermatic diseases, drugs for arrest of bleeding, gout treatment drugs, drugs for diabetes, drugs for anti-malignant tumor, antibiotics, chemical therapy drugs, narcotics, quit smoking aids and the like.

While the content of the drug is not particularly limited as long as it satisfies an effect of transdermally absorbable drugs and does not impair the adhesion property of the adhesive, it is, for example, 0.5-50 parts by weight per 60 parts by weight of the basic polymer.

The adhesive layer may contain, where necessary, other additives known per se, such as anti-aging agent, antioxidant, UV absorber, filler and the like.

The thickness of the adhesive layer is preferably 10 μm-1000 μm, particularly preferably 20 μm-500 μm, from the aspects of skin adhesiveness.

While the production methods of the patch and patch preparation are not particularly limited, the patch and patch preparation can be produced by, for example, the following methods.

A method comprising (i) a step of dissolving or dispersing a basic polymer having a butadiene skeleton and, where necessary, a tackifier, an organic liquid component, a drug and the like in a solvent, adding organic peroxide and mixing and stirring the mixture; (ii) a step of applying the obtained adhesive solution or dispersion to at least one surface of a support, and drying to form the adhesive layer on the surface of the support; and (iii) a step of forming a release liner on the adhesive layer (i.e., direct coating).

Alternatively, a method comprising (i) a step of applying the above-mentioned adhesive solution or dispersion to at least one surface of a release liner for protection; (ii) a step of drying to form the adhesive layer on the surface of a release liner; (iii) a step of adhering a support to the adhesive layer (i.e., indirect coating).

To promote crosslinking of the basic polymer in the adhesive layer, the above-mentioned methods preferably further include, for example, a maturing step. A maturing step can be performed by, for example, heating and preserving at 50-300° C. for 10-100 hr.

EXAMPLES

The present invention is explained in more detail in the following by referring to Examples, which are not to be construed as limitative.

Example 1

Under an air atmosphere, polybutadiene (weight average molecular weight 458,000, 35 parts by weight) as a basic polymer, an alicyclic saturated hydrocarbon resin (softening point 100.5° C., 35 parts by weight) as a tackifier and isopropyl myristate (30 parts by weight) as an organic liquid component were added to toluene, and the mixture was stirred. Dibenzoyl peroxide as organic peroxide was added to the obtained mixture such that the amount relative to 100 parts by weight of the basic polymer was 0.2 part by weight and the mixture was further stirred to give an adhesive solution. The mixing ratio in each Example is shown in Table 1. In Table 1, the amount of organic peroxide is shown in parts by weight per 100 parts by weight of the basic polymer.

Then, the solid content of the adhesive solution was adjusted to 25-40 wt %, the adjusted adhesive solution was applied to a polyester release liner (75 μm thick) such that the thickness after drying was 100 μm and dried to give an adhesive layer.

A laminate film of a polyester film (2 μm thick) and a polyester non-woven fabric (fabric weight 8 g/m$^2$) was used as a support, the above-mentioned adhesive layer was transferred onto the non-woven fabric surface of the support to give a laminate, which was heated and aged in the presence of nitrogen to give a patch.

Example 2

In the same manner as in Example 1 except that 0.3 part by weight of dibenzoyl peroxide was used instead of 0.2 part by weight thereof, a patch was prepared.

Example 3

In the same manner as in Example 1 except that 0.35 part by weight of dibenzoyl peroxide was used instead of 0.2 part by weight thereof, a patch was prepared.

Example 4

In the same manner as in Example 1 except that 0.4 part by weight of dibenzoyl peroxide was used instead of 0.2 part by weight thereof, a patch was prepared.

Example 5

In the same manner as in Example 2 except that 52.5 parts by weight of polybutadiene was used instead of 35 parts by weight thereof and 17.5 parts by weight of alicyclic saturated hydrocarbon resin was used instead of 35 parts by weight thereof, a patch was prepared.

Example 6

In the same manner as in Example 5 except that 0.4 part by weight of dibenzoyl peroxide was used instead of 0.3 part by weight thereof, a patch was prepared.

Example 7

In the same manner as in Example 2 except that 46.7 parts by weight of polybutadiene was used instead of 35 parts by weight thereof and 23.3 parts by weight of alicyclic saturated hydrocarbon resin was used instead of 35 parts by weight thereof, a patch was prepared.

Example 8

In the same manner as in Example 2 except that 31.1 parts by weight of polybutadiene was used instead of 35 parts by weight thereof and 38.9 parts by weight of alicyclic saturated hydrocarbon resin was used instead of 35 parts by weight thereof, a patch was prepared.

Example 9

In the same manner as in Example 2 except that 28.0 parts by weight of polybutadiene was used instead of 35 parts by weight thereof and 42 parts by weight of alicyclic saturated hydrocarbon resin was used instead of 35 parts by weight thereof, a patch was prepared.

Example 10

In the same manner as in Example 1 except that 60 parts by weight of polybutadiene was used instead of 35 parts by weight thereof, 20 parts by weight of alicyclic saturated hydrocarbon resin was used instead of 35 parts by weight thereof, and 20 parts by weight of isopropyl myristate was used instead of 30 parts by weight thereof, a patch was prepared.

Comparative Example 1

In the same manner as in Example 10 except that 0 part by weight of dibenzoyl peroxide was used instead of 0.2 part by weight thereof, a patch was prepared.

Comparative Example 2

In the same manner as in Example 10 except that 60 parts by weight of polybutadiene was used instead of polybutadiene and 1 part by weight of dibenzoyl peroxide was used instead of 0.2 part by weight thereof, a patch was prepared.

Experimental Example (1) Adhesive Force

In a room at 23° C., 60% RH, the patch was cut into a test piece having a width 12 mm, length 5 cm, a release liner of the test piece was removed, and a test piece was press-adhered to a phenol resin plate (test plate) by one reciprocation of a 2 kg roller. The plate was stood for 30 min under this environment, and the adhesive force of the test piece was measured by a tensile tester by stretching the test piece at a releasing angle of 180° and a releasing rate of 300 mm/minute. In the destruction mode, cohesive failure was G and interface destruction was K.

Evaluation criteria are as follows.

⊙ extremely sufficient adhesive force (0.6 N/12 mm or above and free of cohesive failure)

○ sufficient adhesive force (0.2 N/12 mm or above and less than 0.6 N/12 mm and free of cohesive failure)

Δ A rather weak adhesive force but within tolerable range (less than 0.2 N/12 mm and free of cohesive failure)

× weak adhesive force (cohesive failure)

(2) Retaining Force

In a room at 23° C., 60% RH, the patch was cut into a test piece having a width 10 mm, length 5 cm, a release liner of the test piece was removed, and a test piece was press-adhered to a phenol resin plate (test plate) by one reciprocation of a 2 kg roller. The adhered area then was set to 200 mm2. The plate was stood for 20 min under 40° C. environment and, under 40° C. environment, the surface of the test plate, to which the test piece was not adhered, was fixed so that the test plate would be perpendicular to the floor, a 300 g load was hung from the test piece and the time up to a fall of the test piece from the test plate was evaluated as retaining force. In the destruction mode, cohesive failure was G, interface destruction was K, and partial cohesive failure was K/G.

Evaluation criteria are as follows.

⊙ adequate cohesion strength (120 min or less, with interface destruction or partial cohesive failure)

○ rather high cohesion strength but sufficient cohesion strength (120 min or longer)

× weak cohesion strength (cohesive failure)

The results of Table 1 reveal that the patches of Examples 1-10 had adhesive force and cohesion strength necessary for patch. In addition, interface destruction between the test plate and the adhesive layer occurred during the adhesive force measurement, and an adhesive residue leaving an adhesive on the test plate was not observed. In contrast, although the patches of Comparative Examples had a low content of the organic liquid component, the adhesive force and cohesion strength were insufficient, interface destruction occurred during the adhesive force measurement, and an adhesive residue leaving an adhesive on the test plate was observed. It was considered that crosslinking of basic polymer did not occur in Comparative Example 1, since organic peroxide was not used. It was also considered that crosslinking did not occur in Comparative Example 2 due to the structure of the basic polymer used.

TABLE 1

| | | composition | | | | | measurement | | | | | |
|---|---|---|---|---|---|---|---|---|---|---|---|---|
| | | | | | organic liquid component (parts by weight) IPM | amount (parts by weight) of organic peroxide per 100 parts by weight of basic polymer | adhesive force [N/12 mm] | | | adhesion [min] | | |
| | basic polymer kind | basic polymer:tackifier (weight ratio) | basic polymer (parts by weight) | tackifier (parts by weight) | | | average | destruction | evaluation | average | destruction | evaluation |
| Ex. 1 | polybutadiene | 1:1 | 35 | 35 | 30 | 0.2 | 1.30 | K | ⊙ | 5.17 | K/G | ⊙ |
| Ex. 2 | polybutadiene | 1:1 | 35 | 35 | 30 | 0.3 | 0.72 | K | ⊙ | 7.40 | K/G | ⊙ |
| Ex. 3 | polybutadiene | 1:1 | 35 | 35 | 30 | 0.35 | 0.64 | K | ⊙ | 10.10 | K/G | ⊙ |
| Ex. 4 | polybutadiene | 1:1 | 35 | 35 | 30 | 0.4 | 0.55 | K | ◯ | 24 h.< | — | ◯ |
| Ex. 5 | polybutadiene | 3:1 | 52.5 | 17.5 | 30 | 0.3 | 0.14 | K | Δ | 24 h.< | — | ◯ |
| Ex. 6 | polybutadiene | 3:1 | 52.5 | 17.5 | 30 | 0.4 | 0.16 | K | Δ | 24 h.< | — | ◯ |
| Ex. 7 | polybutadiene | 2:1 | 46.7 | 23.3 | 30 | 0.3 | 1.42 | K | ⊙ | 103.10 | K/G | ⊙ |
| Ex. 8 | polybutadiene | 1:1.25 | 31.1 | 38.9 | 30 | 0.3 | 0.80 | K | ⊙ | 2.70 | K/G | ⊙ |
| Ex. 9 | polybutadiene | 1:1.5 | 28.0 | 42.0 | 30 | 0.3 | 0.83 | K | ⊙ | 2.90 | K/G | ⊙ |
| Ex. 10 | polybutadiene | 3:1 | 60 | 20 | 20 | 0.2 | 1.59 | K | ⊙ | 24 h.< | — | ◯ |
| Comp. Ex. 1 | polybutadiene | 3:1 | 60 | 20 | 20 | 0 | 1.00 | G | X | 9.90 | G | X |
| Comp. Ex. 2 | polyisobutylene | 3:1 | 60 | 20 | 20 | 1 | 1.74 | G | X | 1.27 | G | X |

Examples 11-20

In the same manner as in the above-mentioned Examples 1-10, except that 1 part by weight is subtracted from 28.0-52.5 parts by weight of each basic polymer in Examples 1-10 and 1 part by weight of indomethacin is added as a drug, the patch preparations of Examples 11-20 are prepared.

The patch preparations of Examples 11-20 have the properties similar to those of the patches of the above-mentioned Examples 1-10.

INDUSTRIAL APPLICABILITY

The patch of the present invention stably maintains the quality for a long time, is superior in the skin adhesion force, is associated with less adhesive residue on the skin surface, and can also be utilized for the production of a patch preparation.

This application is based on a patent application No. 2008-186561 filed in Japan (filing date: Jul. 17, 2008), the contents of which are incorporated in full herein by this reference.

The invention claimed is:

1. A patch preparation comprising a support and an adhesive layer formed on at least one surface of the support, wherein the adhesive layer comprises an elastomer obtained by crosslinking polybutadiene in the presence of organic peroxide, a tackifier, an organic liquid component, and a drug, wherein the content of organic peroxide is 0.15-0.375 parts by weight per 100 parts of polybutadiene, and the ratio of the weight (a) of polybutadiene to the weight (b) of the tackifier ((a):(b)) is 3.0:1-1:2.0.

* * * * *